United States Patent [19]

Engel et al.

[11] Patent Number: 5,006,522
[45] Date of Patent: Apr. 9, 1991

[54] CONDENSED DIAZEPINONES, PROCESSES FOR PREPARING THEM AND PHARMACEUTICAL COMPOSITIONS CONTAINING THESE COMPOUNDS

[75] Inventors: Wolfhard Engel; Wolfgang Eberlein; Gerhard Mihm; Gunther Trummlitz; Norbert Mayer, all of Biberach, Fed. Rep. of Germany; Adriaan De Jonge, Driebergen, Netherlands

[73] Assignee: Karl Thomae GmbH, Biberach an der Riss, Fed. Rep. of Germany

[21] Appl. No.: 358,740

[22] Filed: May 30, 1989

[30] Foreign Application Priority Data

May 30, 1988 [DE] Fed. Rep. of Germany ....... 3818299

[51] Int. Cl.$^5$ .................... A61K 31/55; C07D 521/00
[52] U.S. Cl. ................................. 514/221; 540/495
[58] Field of Search .................... 540/495; 514/221

[56] References Cited

U.S. PATENT DOCUMENTS 3,105,125  9/1964  Schmutz et al. ............... 540/495
4,749,788  6/1988  Lo et al. ........................ 540/495

FOREIGN PATENT DOCUMENTS 0213293  6/1986  European Pat. Off. ........... 540/495
911m    12/1961  France ........................... 540/495

OTHER PUBLICATIONS

Albert, "Ber. Dtsch Chem Ges.", vol. 42, pp. 545–556 (1909).
Von Braun et al., "Ber. Dtsch. Chem. Ges.", vol. 87, pp. 185–191 (1924).
McCasland et al., "J. Org. Chem.", vol. 22, pp. 122–126 (1956).
Solov'ev et al., "J. Gen. Chem. USSR", vol. 32, pp. 432–437 (1962).
Canellin et al., "J. Chem. Soc. (C)", pp. 2220–2225 (1967).
Herbert et al., "J. Med Chem.", vol. 30, pp. 2081–2086 (1987).
Beilstein, "Handbuch der Organischen Chemie", Band 4, E, p. 378 (1927).
Beilstein, "Handbuch der Organischen Chemie", Band 4 E III, p. 306, (1927).

Primary Examiner—Robert T. Bond
Attorney, Agent, or Firm—David E. Frankhouser; Daniel Reitenbach; Mary-Ellen M. Timbers

[57] ABSTRACT

Novel condensed diazepinone of general formula I are described,

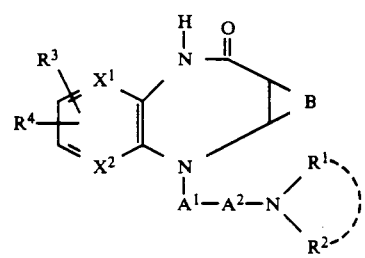

wherein B represents one of the divalent groups

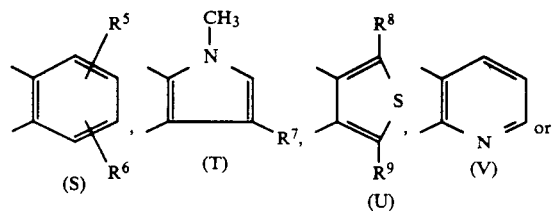

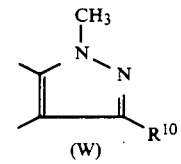

and $X^1$, $X^2$, $A^1$, $A^2$ and $R^1$ to $R^{10}$ are as defined in herein useful as vagal pacemakers for treating bradycardia and bradyarrhythmia. The novel diazepinones also have spasmolytic properties on peripheral organs, antiemetic properties and are capable of promoting cerebral blood flow.

17 Claims, No Drawings

CONDENSED DIAZEPINONES, PROCESSES FOR PREPARING THEM AND PHARMACEUTICAL COMPOSITIONS CONTAINING THESE COMPOUNDS

The invention relates to new condensed diazepinones, processes for preparing them and pharmaceutical compositions containing these compounds.

Condensed diazepinones with anti-ulcerative properties and an inhibitory effect on gastric juice secretion are already known from EP-A-0 039 519 and 0 057 428 and from U.S. Pat. Nos. 3,660,380; 3,691,159; 4,213,984; 4,213,985; 4,210,648; 4,410,527; 4,424,225; 4,424,222 and 4,424,226.

EP-A-0 156 191 describes how completely different, valuable pharmacological properties compared with the compounds of the above-mentioned publications can be induced by introducing new aminoacyl groups. The condensed diazepinones according to the invention are surprisingly distinguished from these compounds by a substantially more powerful effect and marked stability to hydrolysis, whilst having a comparable or better selectivity and resorption after oral administration.

The new condensed diazepinones have the general formula I,

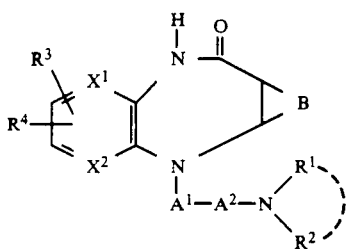

wherein

B represents one of the divalent groups

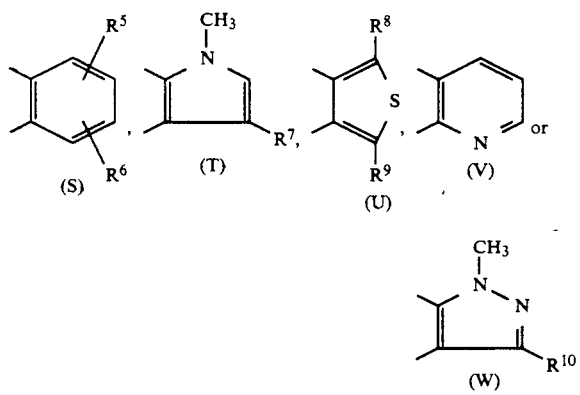

and $X^1$, $X^2$, $A^1$, $A^2$ and $R^1$ to $R^{10}$ are defined as follows:

$X^1$ and $X^2$ represent a =CH group or, if B assumes the definitions of the divalent groups (S), (U) or (W) mentioned above, both or only $X^1$ or only $X^2$ may also represent a nitrogen atom;

$A^1$ is a methylene group optionally substituted by one or two methyl groups;

$A^2$ is a straight-chained alkylene chain optionally containing a double or triple bond and comprising from 3 to 7 carbon atoms, which may additionally be methyl-substituted;

$R^1$ is a branched or unbranched alkyl group with 1 to 4 carbon atoms;

$R^2$ is a branched or unbranched alkyl group with 1 to 7 carbon atoms which may optionally also be substituted by a hydroxy group at its 2nd to 7th carbon atoms, or it represents a cycloalkyl or cycloalkylmethyl group with 3 to 7 carbon atoms in the ring, whilst the cycloalkyl ring may optionally also be substituted by a hydroxy group;

$R^1$ and $R^2$ together with the intervening nitrogen atom, may however also form a 4- to 7-membered saturated, monocyclic, heterocyclic ring which may optionally be interrupted by an oxygen atom or a nitrogen function and/or may be substituted by an alkyl group itself optionally substituted by a phenyl, dialkylamino or (cycloalkyl)alkylamino group or by a (cycloalkyl)alkyl group optionally containing one or two etheric-oxygen atoms, whilst the above-mentioned cycloalkyl groups may contain 4 to 7 carbon atoms;

$R^3$ is an alkyl group with 1 to 4 carbon atoms, a chlorine atom or a hydrogen atom;

$R^4$ is a hydrogen atom or a methyl group;

$R^5$ and $R^6$ each represents a hydrogen atom, a fluorine, chlorine or bromine atom or an alkyl group with 1 to 4 carbon atoms;

$R^7$ represents a hydrogen or chlorine atom or a methyl group;

$R^8$ represents a hydrogen atom or an alkyl group with 1 to 4 carbon atoms;

$R^9$ represents a hydrogen or halogen atom or an alkyl group with 1 to 4 carbon atoms and $R^{10}$ represents a hydrogen atom or a methyl group.

If B represents the divalent group T and $R^7$ is a hydrogen atom, $R^3$ cannot represent a chlorine atom and $A^2$ cannot contain any double or triple bonds.

Preferred compounds of general formula I above are those wherein $X^1$ is a =CH— group, $X^2$ either represents a nitrogen atom and B represents the divalent group (S) with the proviso that $R^3$, $R^4$ and $R^5$ are hydrogen atoms and $R^6$ is a hydrogen atom, a chlorine or bromine atom or a methyl or ethyl group in the 8 or 9-position of the heterocyclic group, or represents a =CH— group, if B assumes the meaning of the divalent groups U or V, whilst $R^8$ is a hydrogen atom and $R^9$ is a methyl group;

$A^1$ is the methylene group;

$A^2$ is a straight-chained alkylene chain optionally containing a double or triple bond and comprising 3 to 6 carbon atoms;

$R^1$ is a branched or unbranched alkyl group with 1 to 4 carbon atoms;

$R^2$ is a branched or unbranched alkyl group with 1 to 7 carbon atoms, a cycloalkyl or (cycloalkyl)methyl group with 3 to 7 carbon atoms in the ring, whilst the cycloalkyl ring may optionally also be substituted by a hydroxy group, or $R^1$ and $R^2$ together with the intervening nitrogen atom form a 5- to 7-membered saturated, monocyclic, heterocyclic ring which may optionally be interrupted by an oxygen atom or a nitrogen atom and/or substituted by an alkyl group optionally substituted by a phenyl, dialkylamino or (cycloalkyl)alkylamino group or by a (cycloalkyl)alkyl group optionally containing one or two etheric-oxygen atoms, whilst the above-mentioned cycloalkyl groups may contain 4 to 7 carbon atoms.

Particularly preferred compounds of general formula I are those wherein $X^1$ is a =CH— group, $X^2$ represents a nitrogen atom and B represents the divalent group (S), with the proviso that $R^3$, $R^4$ and $R^5$ are hydrogen atoms and $R^6$ is a hydrogen, chlorine or bromine atom or a methyl or ethyl group in the 8- or 9-position of the heterocycle, $A^1$ represents a methylene group, $A^2$ represents a straight-chained alkylene chain optionally containing a double or triple bond and comprising three to six carbon atoms and $R^1$ and $R^2$ together with the intervening nitrogen atom represent a dimethylamino, diethylamino, dipropylamino, [bis(methylethyl)]amino, 1-pyrrolidinyl, 1-piperidinyl, hexahydro-1H-1-azepinyl, 4-morpholinyl, 2-[(diethylamino)methyl]-1-piperidinyl, trans-(4-hydroxycyclohexyl)methylamino, (cyclohexyl)methylamino, 2-[[(cyclohexyl)methylamino]methyl]-1-piperidinyl, 4-methyl-1-piperazinyl, 4-[2-(1,3-dioxolan-2-yl)ethyl]-1-piperazinyl, 4-(phenylmethyl)-1-piperazinyl or 4-(2-phenylethyl)-1-piperazinyl group.

After being reacted with inorganic or organic acids the compounds of general formula I may also occur in the form of their physiologically acceptable salts. Suitable acids include, for example, hydrochloric, hydrobromic, sulphuric, methylsulphuric, phosphoric, tartaric, fumaric, citric, maleic, succinic, gluconic, malic, p-toluenesulphonic, methanesulphonic, amidosulphonic or cyclohexanesulphamic acids.

To illustrate the object of the invention, the following compounds may be mentioned by way of example:

5,11-dihydro-11-[4-(1-pyrrolidinyl)-but-2-ynyl]-6H-pyrido[2,3-b][1,4]benzodiazepin-6-one;

5,11-dihydro-11-[4-(dimethylamino)-but-2-ynyl]-6H-pyrido[2,3-b][1,4]benzodiazepin-6-one;

11-[4-(diethylamino)-but-2-ynyl]-5,11-dihydro-6H-pyrido[2,3-b][1,4]benzodiazepin-6-one;

11-[4-[bis(methylethyl)amino]-but-2-ynyl]-5,11-dihydro-6H-pyrido[2,3-b][1,4]benzodiazepin-6-one;

11-[4-[(cyclohexyl)methylamino]-but-2-ynyl]-5,11-dihydro-6H-pyrido[2,3-b][1,4]benzodiazepin-6-one;

11-[4-[2-[(diethylamino)methyl]-1-piperidinyl]-but-2-ynyl]-5,11-dihydro-6H-pyrido[2,3-b][1,4]benzodiazepin-6-one;

5,11-dihydro-11-[4-[2-[(dipropylamino)methyl]-1-piperidinyl]-but-2-ynyl]-6H-pyrido[2,3-b][1,4]benzodiazepin-6-one;

trans-5,11-dihydro-11-[4-[(4-hydroxycyclohexyl)methylamino]-but-2-ynyl]-6H-pyrido[2,3-b][1,4]benzodiazepin-6-one;

5,11-dihydro-11-[4-(1-piperidinyl)-but-2-ynyl]-6H-pyrido[2,3-b][1,4]benzodiazepin-6-one-hemifumarate;

5,11-dihydro-11-[4-(hexahydro-1H-1-azepinyl)-but-2-ynyl]-6H-pyrido[2,3-b][1,4]benzodiazepin-6-one hydrochloride;

5,11-dihydro-11-[4-(4-morpholinyl)-but-2-ynyl]-6H-pyrido[2,3-b][1,4]benzodiazepin-6-one;

11-[4-[2-[[(cyclohexyl)methylamino]methyl]-1-piperidinyl]-but-2-ynyl]-5,11-dihydro-6H-pyrido[2,3-b][1,4]benzodiazepin-6-one;

11-[4-[2-[[(cyclohexyl)methylamino]methyl]-1-piperidinyl]butyl]-5,11-dihydro-6H-pyrido[2,3-b][1,4]benzodiazepin-6-one;

(E)-11-[4-[2-[[(cyclohexyl)methylamino]methyl]-1-piperidinyl]-but-2-enyl]-5,11-dihydro-6H-pyrido[2,3-b][1,4]benzodiazepin-6-one;

(Z)-11-4-[2-[[(cyclohexyl)methylamino]methyl]-1-piperidinyl]-but-2-enyl]-5,11-dihydro-6H-pyrido[2,3-b][1,4]benzodiazepin-6-one;

5,11-dihydro-11-[4-(4-methyl-1-piperazinyl)-but-2-ynyl]-6H-pyrido[2,3-b][1,4]benzodiazepin-6-one;

5,11-dihydro-11-[4-(1-piperidinyl)-butyl]-6H-pyrido[2,3-b][1,4]benzodiazepin-6-one;

5,11-dihydro-11-[5-(1-piperidinyl)-pent-2-ynyl]-6H-pyrido[2,3-b][1,4]benzodiazepin-6-one;

5,11-dihydro-11-[5-(1-piperidinyl)pentyl]-6H-pyrido[2,3-b][1,4]benzodiazepin-6-one;

(E)-5,11-dihydro-11-[5-(1-piperidinyl)-pent-2-enyl]-6H-pyrido[2,3-b][1,4]benzodiazepin-6-one;

(Z)-5,11-dihydro-11-[5-(1-piperidinyl)-pent-2-enyl]-6H-pyrido[2,3-b][1,4]benzodiazepin-6-one;

5,11-dihydro-11-[5-(hexahydro-1H-1-azepinyl)-pent-2-ynyl]-6H-pyrido[2,3-b][1,4]benzodiazepin-6-one;

5,11-dihydro-11-[5-(hexahydro-1H-1-azepinyl)pentyl]-6H-pyrido[2,3-b][1,4]benzodiazepin-6-one;

5,11-dihydro-11-[1-methyl-5-(1-piperidinyl)-pent-2-ynyl]-6H-pyrido[2,3-b][1,4]benzodiazepin-6-one;

5,11-dihydro-11-[1,1-dimethyl-5-(1-piperidinyl)-pent-2-ynyl]-6H-pyrido[2,3-b][1,4]benzodiazepin-6-one;

5,11-dihydro-11-[5-(1-piperidinyl)-hex-2-ynyl]-6H-pyrido[2,3-b][1,4]benzodiazepin-6-one;

5,11-dihydro-11-[5-(1-piperidinyl)-pent-3-ynyl]-6H-pyrido[2,3-b][1,4]benzodiazepin-6-one;

5,11-dihydro-11-[6-(1-piperidinyl)-hex-2-ynyl]-6H-pyrido[2,3-b][1,4]benzodiazepin-6-one;

5,11-dihydro-11-[6-(1-piperidinyl)-hexyl]-6H-pyrido[2,3-b][1,4]benzodiazepin-6-one;

(E)-5,11-dihydro-11-[6-(1-piperidinyl)-hex-2-enyl]-6H-pyrido[2,3-b][1,4]benzodiazepin-6-one;

(Z)-5,11-dihydro-11-[6-(1-piperidinyl)-hex-2-enyl]-6H-pyrido[2,3-b][1,4]benzodiazepin-6-one;

5,11-dihydro-11-[6-(hexahydro-1H-1-azepinyl)-hex-2-ynyl]-6H-pyrido[2,3-b][1,4]benzodiazepin-6-one;

5,11-dihydro-11-[1-methyl-6-(1-piperidinyl)-hex-2-ynyl]-6H-pyrido[2,3-b][1,4]benzodiazepin-6-one;

5,11-dihydro-11-[1,1-dimethyl-6-(1-piperidinyl)-hex-2-ynyl]-6H-pyrido[2,3-b][1,4]benzodiazepin-6-one;

5,11-dihydro-11-[6-(1-piperidinyl)-hept-2-ynyl]-6H-pyrido[2,3-b][1,4]benzodiazepin-6-one;

5,11-dihydro-11-[6-(1-piperidinyl)-hex-3-ynyl]-6H-pyrido[2,3-b][1,4]benzodiazepin-6-one;

5,11-dihydro-11-[6-(1-piperidinyl)-hex-4-ynyl]-6H-pyrido[2,3-b][1,4]benzodiazepin-6-one;

5,11-dihydro-11-[6-(4-methyl-1-piperazinyl)hexyl]-6H-pyrido[2,3-b][1,4]benzodiazepin-6-one;

5,11-dihydro-11-[6-(hexahydro-1H-1-azepinyl)hexyl]-6H-pyrido[2,3-b][1,4]benzodiazepin-6-one;

5,11-dihydro-11-[6-(1-pyrrolidinyl)hexyl]-6H-pyrido[2,3-b][1,4]benzodiazepin-6-one;

(E)-5,11-dihydro-11-[6-(1-piperidinyl)-hex-3-enyl]-6H-pyrido[2,3-b][1,4]benzodiazepin-6-one;

(Z)-5,11-dihydro-11-[6-(1-piperidinyl)-hex-3-enyl]-6H-pyrido[2,3-b][1,4]benzodiazepin-6-one;

(E)-5,11-dihydro-11-[6-(1-piperidinyl)-hex-4-enyl]-6H-pyrido[2,3-b][1,4]benzodiazepin-6-one; (Z)-5,11-dihydro 11-[6-(1-piperidinyl)-hex-4-enyl]-6H-pyrido[2,3-b][1,4]benzodiazepin-6-one;

D,L-11-[6-[2-[(diethylamino)methyl]-1-piperidinyl]hexyl]-5,11-dihydro-6H-pyrido[2,3-b][1,4]benzodiazepin-6-one;

(R)-11-[6-[2-[(diethylamino)methyl]-1-piperidinyl]hexyl]-5,11-dihydro-6H-pyrido[2,3-b][1,4]benzodiazepin-6-one;

(S)-11-[6-[2-[(diethylamino)methyl]-1-piperidinyl]hexyl]-5,11-dihydro-6H-pyrido[2,3-b][1,4]benzodiazepin-6-one;

5,11-dihydro-11-[7-(1-piperidinyl)heptyl]-6H-pyrido[2,3-b][1,4]benzodiazepin-6-one;

5,11-dihydro-11-[7-(1-piperidinyl)octyl]-6H-pyrido[2,3-b][1,4]benzodiazepin-6-one;

5,11-dihydro-11-[7-(1-piperidinyl)-hept-2-ynyl]-6H-pyrido[2,3-b]1,4]benzodiazepin-6-one;

5,11-dihydro-11-[7-(1-piperidinyl)-hept-3-ynyl]-6H-pyrido[2,3-b][1,4]benzodiazepin-6-one;

5,11-dihydro-11-[7-(1-piperidinyl)-hept-4-ynyl]-6H-pyrido[2,3-b][1,4]benzodiazepin-6-one;

5,11-dihydro-11-[7-(1-piperidinyl)-hept-5-ynyl]-6H-pyrido[2,3-b][1,4]benzodiazepin-6-one;

5,11-dihydro-11-[1-methyl-7-(1-piperidinyl)heptyl]-6H-pyrido[2,3-b][1,4]benzodiazepin-6-one; 5,11-dihydro-11-[1,1-dimethyl-7-(1-piperidinyl)hept-2-ynyl]-6H-pyrido[2,3-b][1,4]benzodiazepin-6-one;

5,11-dihydro-11-[7-(hexahydro-1H-1-azepinyl)-hept-2-ynyl]-6H-pyrido[2,3-b][1,4]benzodiazepin-6-one;

11-[7-[2-[(diethylamino)methyl]-1-piperidinyl]heptyl]-5,11-dihydro-6H-pyrido[2,3-b][1,4]benzodiazepin-6-one;

5,11-dihydro-11-[4-methyl-7-(1-piperidinyl)heptyl]-6H-pyrido[2,3-b][1,4]benzodiazepin-6-one;

6,11-dihydro-11-[6-[1-piperidinyl]-hex-2-ynyl]-5H-pyrido[2,3-b][1,5]benzodiazepin-5-one;

6,11-dihydro-11-[6-(1-piperidinyl)hexyl]-5H-pyrido[2,3-b][1,5]benzodiazepin-5-one;

(E)-6,11-dihydro-11-[6-(1-piperidinyl)-hex-2-enyl]-5H-pyrido[2,3-b][1,5]benzodiazepin-5-one;

(Z)-6,11-dihydro-11-[6-(1-piperidinyl)-hex-2-enyl]-5H-pyrido[2,3-b][1,5]benzodiazepin-5-one;

6,11-dihydro-11-[6-(hexahydro-1H-1-azepinyl)-hex-2-ynyl]-5H-pyrido[2,3-b][1,5]benzodiazepin-5-one;

6,11-dihydro-11-[1,1-dimethyl-6-(1-piperidinyl)hex-2-ynyl]-5H-pyrido[2,3-b][1,5]benzodiazepin-5-one;

6,11-dihydro-11-[6-(4-methyl-1-piperazinyl)hexyl]-5H-pyrido[2,3-b][1,5]benzodiazepin-5-one;

6,11-dihydro-11-[6-(1-pyrrolidinyl)hexyl]-5H-pyrido[2,3-b][1,5]benzodiazepin-5-one;

5,11-dihydro-2-methyl-11-[6-(1-piperidinyl)hexyl]-6H-pyrido[2,3-b][1,4]benzodiazepin-6-one;

5,11-dihydro-8-methyl-11-[6-(1-piperidinyl)hexyl]-6H-pyrido[2,3-b][1,4]benzodiazepin-6-one;

5,11-dihydro-9-methyl-11-[6-(1-piperidinyl)hexyl]-6H-pyrido[2,3-b][1,4]benzodiazepin-6-one;

5,11-dihydro-8-ethyl-11-[6-(1-piperidinyl)hexyl]-6H-pyrido[2,3-b][1,4]benzodiazepin-6-one;

8-chloro-5,11-dihydro-11-[6-(1-piperidinyl)hexyl]-6H-pyrido[2,3-b][1,4]benzodiazepin-6-one;

9-chloro-5,11-dihydro-11-[6-(1-piperidinyl)hexyl]-6H-pyrido[2,3-b][1,4]benzodiazepin-6-one;

9-bromo-5,11-dihydro-11-[6-(1-piperidinyl)hexyl]-6H-pyrido[2,3-b][1,4]benzodiazepin-6-one;

5,11-dihydro-8-fluoro-11-[6-(1-piperidinyl)hexyl]-6H-pyrido[2,3-b][1,4]benzodiazepin-6-one;

5,10-dihydro-5-[6-(1-piperidinyl)hexyl]-11H-dibenzo[b,e][1,4]diazepin-11-one;

5,10-dihydro-5-[6-(4-methyl-1-piperazinyl)hexyl]-11H-dibenzo[b,e][1,4]diazepin-11-one;

5,10-dihydro-5-[6-(hexahydro-1H-1-azepinyl)hexyl]-11H-dibenzo[b,e][1,4]diazepin-11-one hydrochloride;

5,10-dihydro-5-[6-(1-pyrrolidinyl)hexyl]-11H-dibenzo[b,e][1,4]diazepin-11-one hydrochloride;

5,10-dihydro-5-[6-[4-[2-(1,3-dioxolan-2-yl)ethyl]-1-piperazinyl]hexyl]-11H-dibenzo[b,e][1,4]diazepin-11-one;

4,9-dihydro-3-methyl-4-[6-(1-piperidinyl)-hex-2-ynyl]-10H-thieno[3,4-b][1,5]benzodiazepin-10-one;

4,9-dihydro-4-[6-(1-piperidinyl)-hex-2-ynyl]-10H-thieno[3,4-b][1,5]benzodiazepin-10-one;

(E)-4,9-dihydro-3-methyl-4-[6-(1-piperidinyl)-hex-2-enyl]-10H-thieno[3,4-b][1,5]benzodiazepin-10-one;

(Z)-4,9-dihydro-3-methyl-4-[6-(1-piperidinyl)-hex-2-enyl]-10H-thieno[3,4-b][1,5]benzodiazepin-10-one;

4,9-dihydro-4-[6-(hexahydro-1H-1-azepinyl)-hex-2-ynyl]-3-methyl-10H-thieno[3,4-b][1,5]benzodiazepin-10-one;

4,9-dihydro-4-[1,1-dimethyl-6-(1-piperidinyl)-hex-2-ynyl]-3-methyl-10H-thieno[3,4-b][1,5]benzodiazepin-10-one;

4,9-dihydro-3-methyl-4-[6-(4-methyl-1-piperazinyl)hexyl]-10H-thieno[3,4-b][1,5]benzodiazepin-10-one;

4,9-dihydro-3-methyl-4-[6-(1-pyrrolidinyl)hexyl]-10H-thieno[3,4-b][1,5]benzodiazepin-10-one;

3-chloro-4,9-dihydro-4-[6-(1-piperidinyl)-hex-2-ynyl]-10H-thieno[3,4-b][1,5]benzodiazepin-10-one;

1,3-dimethyl-4-[6-(1-piperidinyl)-hex-2-ynyl]-10H-thieno[3,4-b][1,5]benzodiazepin-10-one;

1,3-dimethyl-4-[6-(hexahydro-1H-1-azepinyl)-hex-2-ynyl]-1,4,9,10-tetrahydropyrrolo[3,2-b][1,5]benzodiazepin-10-one;

(E)-1,3-dimethyl-4-[6-(1-piperidinyl)-hex-3-enyl]-1,4,9,10-tetrahydropyrrolo[3,2-b][1,5]benzodiazepin-10-one;

1,3-dimethyl-4-[1,1-dimethyl-6-(1-piperidinyl)-hex-2-ynyl]-1,4,9,10-tetrahydropyrrolo[3,2-b][1,5]-benzodiazepin-10-one;

1,3-dimethyl-4-[6-(4-methyl-1-piperazinyl)hexyl]-1,4,9,10-tetrahydropyrrolo[3,2-b][1,5]benzodiazepin-10-one;

1,3-dimethyl-4-[6-(1-pyrrolidinyl)hexyl]-1,4,9,10-tetrahydropyrrolo[3,2-b][1,5]benzodiazepin-10-one;

3-chloro-1-methyl-4-[6-(1-piperidinyl)-hex-2-ynyl]-1,4,9,10-tetrahydropyrrolo[3,2-b][1,5]benzodiazepin-10-one;

1-methyl-4-[6-(1-piperidinyl)-hex-2-ynyl]-1,4,9,10-tetrahydropyrrolo[3,2-b][1,5]benzodiazepin-10-one;

1,3-dimethyl-4-[6-(1-piperidinyl)-hex-2-ynyl]-1,4,9,10-tetrahydropyrazolo[4,3-b][1,5]benzodiazepin-10-one;

1,3-dimethyl-4-[6-(hexahydro-1H-1-azepinyl)-hex-2-ynyl]-1,4,9,10-tetrahydropyrazolo[4,3-b][1,5]benzodiazepin-10-one;

(Z)-1,3-dimethyl-4-[6-(1-piperidinyl)-hex-2-enyl]-1,4,9,10-tetrahydropyrazolo[4,3-b][1,5]benzodiazepin-10-one;

1,3-dimethyl-4-[1,1-dimethyl-6-(1-piperidinyl)hexyl]-1,4,9,10-tetrahydropyrazolo[4,3-b][1,5]benzodiazepin-10-one;

1,3-dimethyl-4-[6-(4-methyl-1-piperazinyl)-hexyl]-1,4,9,10-tetrahydropyrazolo[4,3-b][1,5]benzodiazepin-10-one;

1,3-dimethyl-4-[6-(1-pyrrolidinyl)-hexyl]-1,4,9,10-tetrahydropyrazolo[4,3-b][1,5]benzodiazepin-10-one;

1-methyl-4-[6-(1-piperidinyl)-hex-2-ynyl]-1,4,9,10-tetrahydropyrazolo[4,3-b][1,5]benzodiazepin-10-one;

4-[6-[2-[(diethylamino)methyl]-1-piperidinyl]-hexyl]-1-methyl-1,4,9,10-tetrahydropyrazolo[4,3-b][1,5]benzodiazepin-10-one.

According to the invention, the new base-substituted condensed diazepinones of general formula I are obtained by the following processes:

(a) Base-substituted condensed diazepinones of general formula I wherein $A^1$, $A^2$, $R^1$, $R^2$, $R^3$, $R^4$, $X^1$ and $X^2$ are as hereinbefore defined and the divalent group B also has the meanings specified, with the restriction that $R^7$ cannot be a hydrogen atom, are obtained by converting tricyclic compounds of general formula II

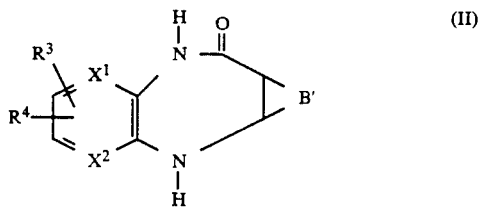

wherein the groups $R^3$, $R^4$, $X^1$ and $X^2$ are as hereinbefore defined and B' represents one of the divalent groups S, U, V, W or T'

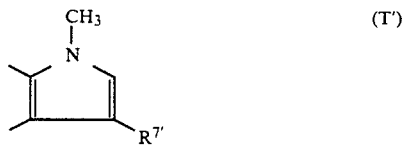

wherein $R^{7'}$ is a chlorine atom or a methyl group, into the corresponding di-lithium salts of general formula III,

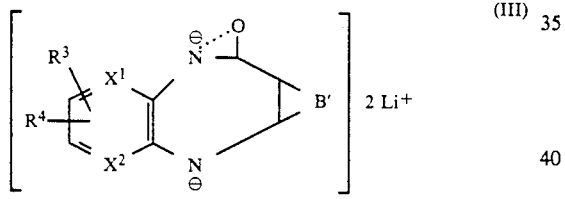

and subsequent alkylation with a compound of general formula IV

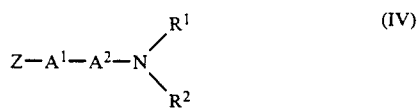

wherein $A^1$, $A^2$, $R^1$ and $R^2$ have the meanings given hereinbefore and Z represents a chlorine, bromine or iodine atom, a methanesulphonyloxy, ethanesulphonyloxy or arenesulphonyloxy group, for example the benzenesulphonyloxy, p-toluenesulphonyloxy or 4-bromobenzenesulphonyloxy group. The reaction is usually carried out as a one-pot process, i.e. the di-lithium salts of general formula III are not isolated but produced in situ and, once formed, reacted further in the same reaction medium.

The conversion of the tricyclic compounds of general formula II into the di-lithium salts of general formula III is carried out by the action of at least 2 mol of a lithium alkyl, particularly n-butyllithium, n-butyllithium in the presence of tetramethylethylenediamine, t-butyllithium, a lithium dialkylamide, more particularly lithium diisopropylamide, lithium dicyclohexylamide, lithium isopropylcyclohexylamide, or lithium aryls, e.g. phenyllithium. The production of the di-lithium salts and the subsequent alkylation are carried out in an organic solvent at temperatures between $-80°$ and $+70°$ C., but preferably between $-10°$ and $+30°$ C. The organic solvents used are those conventionally used for reactions with lithium alkyls, lithium dialkylamides and lithium aryls; it is particularly advantageous to use ethers such as diethyl ether, dioxan or tetrahydrofuran, aliphatic hydrocarbons such as hexane, or mixtures thereof, optionally in the presence of hexamethylphosphoric acid triamide, 1,3-dimethyl-2-imidazolidinone or 1,3-dimethyl-3,4,5,6-tetrahydro-2(1H)-pyrimidinone as cosolvents. Shortly after the addition of the lithium alkyl or lithium aryl has ended, the stoichiometric quantity of the appropriate alkylating agent of general formula IV is added and to complete the reaction the mixture is stirred for some time at ambient temperature.

(b) Base-substituted condensed diazepinones of general formula I wherein $A^1$, $R^1$, $R^2$, $R^3$, $R^4$, $X^1$ and $X^2$ are defined as hereinbefore, $A^2$ represents a straight-chained saturated alkylene chain comprising three to seven carbon atoms which may additionally be methyl-substituted and the divalent group B has the meanings specified hereinbefore, with the restriction that $R^7$ is not a hydrogen atom, are obtained by converting (arylmethyl)tricyclic compounds of general formula V

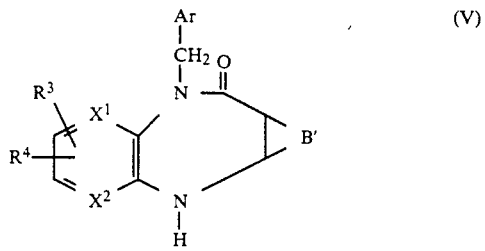

wherein the groups B', $R^3$, $R^4$, $X^1$ and $X^2$ are as hereinbefore defined and Ar represents a phenyl group optionally substituted by one to two methyl and/or methoxy groups, into the corresponding metal salt of general formula Va,

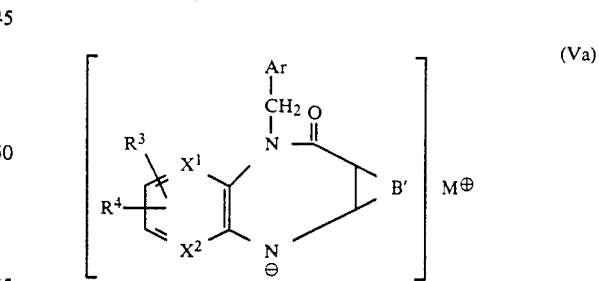

wherein B', $R^3$, $R^4$, $X^1$, $X^2$ and Ar are as hereinbefore defined and M represents an alkali metal, such as lithium, sodium, potassium, rubidium or caesium or represents the group MgHal, wherein Hal is a chlorine, bromine or iodine atom, subsequently alkylating with a compound of general formula IV,

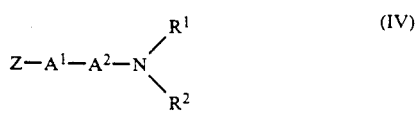

wherein $A^1$, $R^1$, $R^2$ and Z are as hereinbefore defined and $A^2$ represents a straight-chained saturated alkylene chain comprising three to seven carbon atoms, with final acidolytic removal of the arylmethyl group.

The salts of general formula Va are advantageously produced in the reaction mixture immediately before the reaction, for example by the action of lithium alkyls, e.g. n-butyl-lithium, n-butyl-lithium in the presence of tetramethylethylenediamine, t-butyllithium, lithium dialkylamides, e.g. lithium diisopropylamide, lithium dicyclohexylamide and lithium isopropylcyclohexylamide, lithium aryls, such as phenyl lithium, alkali metal hydroxides such as lithium, sodium or potassium hydroxide, alkali metal hydrides such as sodium or potassium hydride or alkali metal amides such as, for example, sodium or potassium amide, or Grignard reagents such as methyl magnesium iodide, ethyl magnesium bromide or phenyl magnesium bromide, on a corresponding (arylmethyl)tricyclic compound of general formula V. The metallisation is conventionally carried out in an inert organic solvent at temperatures of between $-100°$ C. and the boiling point of the reaction mixture in question. If lithium alkyls, lithium aryls, lithium dialkylamides or Grignard reagents are used for the metallisation, the preferred solvents are ethers such as tetrahydrofuran, diethyl ether or dioxan, optionally in admixture with aliphatic or aromatic hydrocarbons, such as hexane or benzene, and the operation is carried out at temperatures of between $-20°$ and $+80°$ C.; when metallisation is effected with alkali metal hydrides and alkali metal amides, in addition to the solvents mentioned hereinbefore it is also possible to use xylene, toluene, acetonitrile, dimethylformamide and dimethylsulphoxide, whilst if alkali metal hydroxides are used it is also possible to use alcohols such as ethanol, methanol and aliphatic ketones such as acetone, as well as mixtures of these solvents with water. The subsequent alkylation with a compound of general formula IV is carried out in a similar way to that described in process a), whilst in order to complete the reaction the mixture may be heated for a longer period to temperatures up to the boiling point of the solvent mixture.

The acidolytic cleaving of the arylmethyl group from the compounds of general formula VI thus obtained,

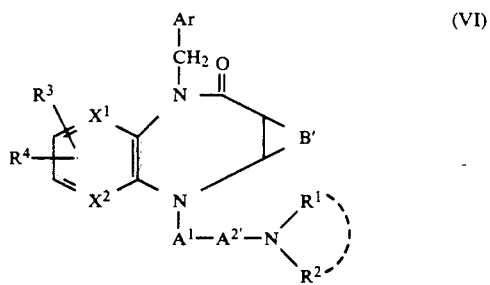

(VI)

(wherein, $A^1$, $R^1$, $R^2$, $R^3$, $R^4$, $X^1$ and $X^2$ are as hereinbefore defined, $A^{2'}$ represents a straight-chained, saturated, alkylene chain comprising three to seven carbon atoms which is optionally methyl-substituted, the divalent group B' has the meanings given for B hereinbefore, with the proviso that $R^7$ is not a hydrogen atom) is effected by reacting with strong acids or Lewis acids and at temperatures of between $-20°$ and $+150°$ C. As strong acids, sulphuric, methanesulphonic, conc. phosphoric but more particularly polyphosphoric acid may be used, and in the event of the use of phosphoric acid and polyphosphoric acid it is particularly useful to add benzene, toluene, phenol, anisole or veratrol in order to pick up the arylmethyl cations formed. If Lewis acids such as aluminium chloride or aluminium bromide are used to remove the arylmethyl group, aromatic hydrocarbons such as benzene, toluene, anisole and mixtures of these aromatic compound with dichloromethane are suitable solvents.

(c) Base-substituted condensed diazepinones of general formula I wherein $A^1$, $R^1$, $R^2$, $R^4$, $X^1$ and $X^2$ are as hereinbefore defined, $A^2$ represents a straight-chained saturated alkylene chain comprising three to seven carbon atoms which may additionally be methyl-substituted, $R^3$ is a hydrogen atom or an alkyl group with 1 to 4 carbon atoms and B represents one of the divalent groups S, T, U or W with the restriction that $R^5$, $R^6$ and $R^7$ do not represent chlorine or bromine atoms, are also obtained by hydrogenolysing compounds of general formula VIa,

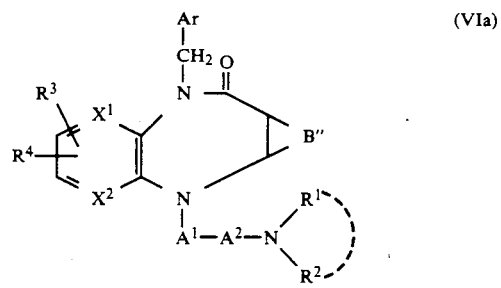

(VIa)

wherein the groups $A^1$, $A^2$, $R^1$, $R^2$, $R^3$, $R^4$, $X^1$, $X^2$ and Ar are as hereinbefore defined and B'' represents one of the divalent groups S, T, U or W with the proviso that $R^7$ is not a hydrogen atom.

The hydrogenolysis is carried out in the presence of catalysts of metals of the VIIIth sub-group of the periodic table of elements, for example palladium on animal charcoal, palladium hydroxide, palladium on barium sulphate, Raney nickel or Raney cobalt, and under hydrogen pressures of from 1 to 300 bar and temperatures of 0° C. to 130° C. in the presence of solvents e.g. alcohols such as methanol or ethanol; ethers such as dioxan, tetrahydrofuran; esters such as ethyl acetate; carboxylic acids, for example acetic acid, mixtures of acetic acid and aceticanhydride and optionally in the presence of inorganic acids, for example hydrochloric acid, phosphoric acid or perchloric acid.

In the starting compounds of general formula VIa, which may be prepared completely analogously to the processes described in b), any chlorine or bromine substituents contained are generally replaced by hydrogen, and any double or triple bonds present in $A^2$ are hydrogenated.

(d) Base-substituted condensed diazepinones of general formula I wherein $A^1$, $R^1$, $R^2$, $R^4$, $X^1$ and $X^2$ are as hereinbefore defined, $A^2$ represents a straight-chained alkylene group optionally containing a double bond and comprising three to seven carbon atoms, which may additionally be methyl-substituted, $R^3$ represents a hydrogen atom or an alkyl group with 1 to 4 carbon atoms and B represents one of the divalent groups S, T, U or W, with the restriction that $R^5$, $R^6$ and $R^7$ do not represent chlorine or bromine atoms, are obtained by catalytic hydrogenation of a compound of general formula VII,

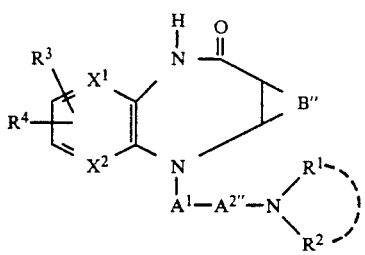 (VII)

wherein the groups $A^1$, $R^1$, $R^2$, $R^3$, $R^4$, $X^1$, $X^2$ and $B''$ are as hereinbefore defined and $A^{2''}$ is a straight-chained alkylene group containing a triple bond and comprising three to seven carbon atoms, which may additionally be methyl-substituted.

The catalytic hydrogenation is carried out in the presence of metals of the VIIIth subgroup of the Periodic Table of Elements, for example palladium on animal charcoal, palladium on barium sulphate, Raney nickel or Raney cobalt, and under hydrogen pressures of from 0.1 to 300 bar and at temperatures of from 0° to 130° C., preferably at ambient temperature, and in the presence of solvents, e.g. alcohols such as methanol or ethanol, ethers such as dioxan, diethyl ether or tetrahydrofuran, carboxylic acids such as acetic acid or tertiary amines such as triethylamine.

In the starting materials of formula VII, any halogen present, with the exception of fluorine, is generally split off during the catalytic hydrogenation.

In order to prepare compounds of formula I wherein $A^2$ represents an alkylene group containing a double bond, the procedure preferably used, starting from a compound of formula VII, is either to stop the catalytic hydrogenation after the uptake of 1 mol of hydrogen and/or to carry out this catalytic hydrogenation in the presence of a deactivated catalyst, e.g. palladium on calcium carbonate deactivated with lead or cadmium (Lindlar catalyst), palladium on barium sulphate with the addition of quinoline or P2-nickel in the presence of ethylenediamine.

Predominantly, compounds of formula I are obtained which are characterised by Z configuration with regard to the olefinic double bond.

Of course, a compound of formula I thus obtained wherein $A^2$ represents an alkylene group containing a double bond can subsequently be further hydrogenated—as described above—to form a compound of formula I wherein $A^2$ represents a saturated alkylene group.

(e) Base-substituted condensed diazepinones of general formula Ia

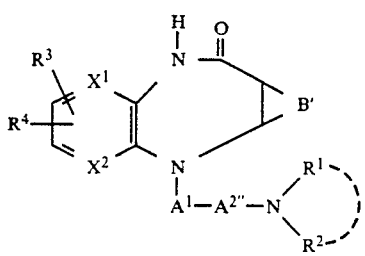 (Ia)

wherein the groups $A^1$, $A^{2''}$, $R^1$, $R^2$, $R^3$, $R^4$, $X^1$, $X^2$ and $B'$ are as hereinbefore defined, which also come under general formula I, are obtained from condensed tricyclic groups of general formula VIII

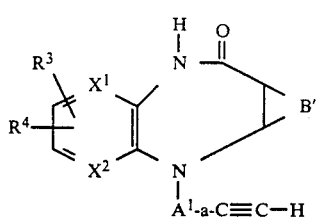 (VIII)

wherein $A^1$, $B'$, $R^3$, $R^4$, $X^1$ and $X^2$ are as hereinbefore defined and "a" represents a single bond or a straight-chained saturated alkylene group with not more than 4 carbon atoms, optionally substituted by a methyl group, by aminoalkylation with compounds of general formula IX

 (IX)

wherein $R^1$, $R^2$ and Z are as hereinbefore defined and "b" represents a straight-chained saturated alkylene group with 1 to 4 carbon atoms in the chain, optionally substituted by a methyl group.

The aminoalkylation is, under certain circumstances, advantageously carried out after previous metallisation and/or in the presence of catalytically active copper compounds.

If, for example, it is desired to introduce the (dialkylamino)methyl or 1-(dialkylamino)-ethyl group into a 1-alkyne of general formula VIII, the starting material of general formula VIII is heated in a polar solvent with formaldehyde or paraformaldehyde or acetaldehyde or paraldehyde or metaldehyde and a secondary amine of general formula X

 (X)

wherein $R^1$ and $R^2$ are as hereinbefore defined. Preferably, the reaction is carried out in the presence of copper salts, for example copper(I) chloride, copper(I) bromide, copper(I) iodide, copper(II)-acetate or copper(II) sulphate. Examples of polar solvents include dimethylformamide, dimethylacetamide, tetrahydrofuran, 1,4-dioxan, dibutyl ether, tert.butanol or mixtures thereof with water. Suitable reaction temperatures range from 20° C. to the boiling point of the reaction mixture. The most favourable yields are achieved in a weakly alkaline reaction medium at a pH of about 9. The active agent of this reaction is the alpha-amino alcohol of formula IXa, which is generally not isolated,

 (IXa)

wherein $R^1$ and $R^2$ are as hereinbefore defined and $R^{11}$ is the hydrogen atom or the methyl group. Instead of a mixture of formaldehyde or acetaldehyde and a secondary amine of general formula X, it is also possible to use the diamines of general formula IXb

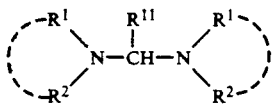

(which are known from the literature or easily obtainable analogously to methods which have already been described) or alpha-alkoxyamines of formula IXc,

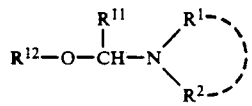

wherein $R^1$, $R^2$ and $R^{11}$ are as hereinbefore defined and $R^{12}$ represents an alkyl group with 1 to 10 carbon atoms. During the reaction with alpha-alkoxyamines of formula IXc, the starting compound of general formula VIII is preferably used as a Grignard compound of general formula VIIIa given below, wherein M=MgHal.

In order to alkylate compounds of general formula IX wherein b represents an optionally methyl-substituted 1,2-ethylene, 1,3-propylene or 1,4-butylene group, the starting materials of general formula VIII are first converted into metal salts of general formula VIIIa,

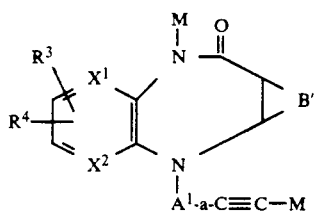

wherein

"a", $A^1$, $B'$, $R^3$, $R^4$, $X^1$ and $X^2$ are as hereinbefore defined and

M represents an alkali metal atom, preferably lithium, or the group MgHal, wherein Hal is a chlorine, bromine or iodine atom, and they are then reacted, without isolation, with the alkylating agents of general formula IX. For lithiation, exactly 2 mol of the metallising reagent are used, such as lithium alkyls, for example n-butyl-lithium, n-butyl-lithium in the presence of tetramethylethylenediamine, tert.butyl-lithium or methyl-lithium, lithium amides, such as lithium diisopropylamide, lithium amide, lithium dicyclohexylamide or lithium isopropylcyclohexylamide, lithium aryls, such as phenyl-lithium, or metallic lithium, possibly in the presence of phenanthrene. If in formula VIIIa M is intended to represent the group MgHal, the 1-alkynes of general formula VIII are reacted with at least 2 mol of a Grignard reagent, e.g. methyl magnesium iodide, ethyl magnesium bromide or phenyl magnesium bromide. The metallisation and subsequent aminoalkylation is usually carried out in an organic solvent and at temperatures ranging from −80° C. to +150° C., preferably from −40° C. to +140° C. The organic solvents used are those conventionally used in reactions with organolithium and organomagnesium compounds; it is particularly advantageous to use ethers such as diethyl ether, tetrahydrofuran, dioxan or 1,2-dimethoxyethane, and liquid ammonia, optionally in admixture, and using polar cosolvents, such as hexamethylphosphoric acid triamide, dimethylsulphoxide, 1,3-dimethyl-2-imidazolidinone or 1,3-dimethyl-3,4,5,6-tetrahydro-2(1H)-pyrimidinone. As a rule, the addition of catalysts, particularly anhydrous copper(I) salts, such as copper-(I)chloride, copper(I) iodide, copper(I)iodide in the presence of lithium or sodium iodide, and copper(I)-cyanide, has the effect of accelerating the reaction.

The base-substituted condensed diazepinones of general formula I according to the invention contain up to three chiral centres in the side chain and may therefore possibly occur in up to four diastereoisomeric forms which may in turn be separated into (+)- and (−)-enantiomers. Diastereomeric cis/trans forms are also possible if $A^2$ in the compounds of general formula I claimed represents an alkylene group containing an olefinic double bond. Compounds of general formula I containing only one chiral centre occur as racemates which can be resolved into the (+)- and (−)-antipodes.

The invention includes the individual isomers as well as the mixtures thereof. The diastereomers can be separated on the basis of their different physico-chemical properties, e.g. by fractional recrystallisation from suitable solvents, by high pressure liquid chromatography, column chromatography or gas chromatography.

Any racemates of the compounds of general formula I may be cleaved by known methods, for example using an optically active acid such as (+)- or (−)-tartaric acid or a derivative thereof such as (+)- or (−)-diacetyltartaric acid, (+)- or (−)-monomethyltartrate or (+)-camphorsulphonic acid.

According to a conventional method of enantiomer separation, the racemate of a compound of general formula I is reacted with one of the above-mentioned optically active acids in equimolar amounts in a solvent and the crystalline diastereomeric salts obtained are separated on the basis of their different solubilities. This reaction may be carried out in any kind of solvent provided that it shows a sufficiently great difference in the solubilities of the salts. It is preferable to use methanol, ethanol or mixtures thereof, e.g. in a ratio by volume of 50:50. Then each of the optically active salts is dissolved in water, neutralised with a base such as sodium carbonate or potassium carbonate and in this way the corresponding free compound is obtained in the (+)- or (−)-form.

Only one enantiomer of the compounds of general formula I is obtained if the methods of synthesis described above are carried out with only one enantiomer of general formulae IV, VI, VIa, VIII, VIIIa or IX.

The tricyclic compounds of general formula II are known from the patent literature or may be synthesised from common starting materials by closely following the published methods.

The starting compounds of general formula IV are known from the literature or obtainable by closely following the methods already described. For example, the aminoalcohols of general formula IVa

wherein $A^1$, $A^2$, $R^1$ and $R^2$ are as hereinbefore defined, can be converted by treatment with concentrated hydrochloric acid or thionyl chloride, with concentrated hydrobromic acid or thionyl bromide, hydriodic acid or methanesulphonic acid, ethanesulphonic acid or arenesulphonic acid derivatives, preferably the corresponding sulphonic acid chlorides or bromides, into compounds of general formula IV wherein Z represents a chlorine, bromine or iodine atom or a methanesulphonyloxy, ethanesulphonyloxy or arenesulphonyloxy group. However, the compounds of general formula IV may also be obtained by alkylating secondary amines of general formula X with a bifunctional compound of general formula IVb $$Z-A^1-A^2-Z' \qquad (IVb)$$

wherein $A^1$, $A^2$ and Z are as hereinbefore defined and Z', which may be identical to or different from Z, may have the same meanings as Z.

The starting compounds of general formula V are synthesised, using methods known from the literature, by arylmethylation of tricyclic compounds of general formula II in the presence of bases, e.g. sodium hydride, potassium carbonate, sodium carbonate, sodium hydroxide or triethylamine (see also: German Auslegeschrift 24 24 811 of 22.05.1974/18.12.1975/02.10.1980).

Starting compounds of general formula VIa are obtained totally analogously to the compounds of general formula VI.

Starting compounds of general formula VII are a sub-group of the compounds of general formula I and may be obtained, for example, by processes (a) and (e) described hereinbefore.

The starting compounds of general formula VIII can easily be prepared from the di-lithium salts of general formula III by alkylation with halides of general formula XI, $$Hal-A^1-a-C \equiv C-H \qquad (XI)$$

wherein $A^1$ and a are as hereinbefore defined and Hal represents a chlorine, bromine or iodine atom. The starting compounds of general formula XI are commercially obtainable or known from the literature (see for example: K. E. Schulte and K.Th. Reiss, Chem. Ber. 86, 777–781 [1953]) or can easily be prepared using methods known from the literature.

The starting compounds of general formula IX are also commercially available or can easily be synthesised from commercial precursors using known methods.

The starting compounds of general formula X are commercially available or known (see for example: DE-A-36 26 095).

The starting compounds of general formulae IXb and IXc are obtainable by a known method from secondary amines of general formula X and formaldehyde or acetaldehyde, or from amines of general formula X, formaldehyde or acetaldehyde, as well as alcohols of general formula XII, $$R^{12}-OH \qquad (XII)$$

wherein $R^{12}$ is defined as hereinbefore.

The base-substituted condensed diazepinones of general formula I and the acid addition salts thereof have valuable properties; in particular, whilst possessing total stability to hydrolysis, high selectivity and good resorption after oral administration, they have favourable effects on heart rate and, in view of the absence of mydriatic effects and inhibitory effects on the secretion of gastric acid and saliva, they are suitable as vagal pacemakers for treating bradycardia and bradyarrhythmia in both human and veterinary medicine; some of the compounds also show spasmolytic properties on peripheral organs, particularly the colon and bladder. In view of their antiemetic properties, some of the compounds of general formula I are also suitable for preventing travel sickness and seasickness and in view of their favourable effects on cerebral blood flow they are useful in geriatric medicine and for the treatment of migraine. The compounds also generally exhibit a good CNS activity, in view of their high lipophilicity, and are therefore useful for the treatment of diseases of the central nervous system, particularly Alzheimer's disease and Parkinson's disease; in Alzheimer's disease, the compounds influence the self-regulatory function of presynaptic muscarinic receptors in response to the release of acetylcholine and consequently lead to a reinforcing of the impulse pattern of the cholinergic fibres still present; in Parkinson's disease, the advantage of using compounds of general formula I instead of the non-selective antimuscarinics used hitherto is the former's absence of non-tolerable peripheral and central atropine-like side-effects.

A favourable relation between tachycardiac effects on the one hand and on the other hand the undesirable effects on pupil size and the secretion of tears, saliva and gastric acid which occur in therapeutic agents with an anticholinergic component is of particular importance in the therapeutic use of the substances. The following tests show that the compounds according to the invention show surprisingly good relations of this kind.

A. Studies of binding to muscarinic receptors

In vitro measurement of the $IC_{50}$ value

The organs were donated by male Sprague-Dawley rats weighing 180–220 g After the heart and submandibular gland and cerebral cortex had been removed, all other steps were carried out in ice-cold Hepes HCl buffer (pH 7.4; 100 millimolar NaCl, 10 millimolar $MgCl_2$). The whole heart was cut up with scissors. All the organs were then homogenised in a Potter apparatus.

For the binding test the homogenised organs were diluted as follows:

| | |
|---|---|
| Whole heart | 1:400 |
| Cerebral cortex | 1:3000 |
| Submandibular gland | 1:400 |

The homogenised organs were incubated at a given concentration of the radioligand and at a series of concentrations of the non-radioactive test substances in an Eppendorf centrifuge tube at 30° C. Incubation lasted 45 minutes. The radioligand used was 0.3 nanomolar $^3$H-N-methylscopolamine ($^3$H-NMS). Incubation was ended by the addition of ice-cold buffer followed by vacuum filtration. The filters were rinsed with cold buffer and their radioactivity was determined. This represents the sum of specific and non-specific binding of $^3$H-NMS. The proportion of non-specific binding was defined as the radioactivity which was bound in the presence of 1 micromolar quinuclidinylbenzylate. Each measurement was taken four times. The $IC_{50}$ values of the non-labelled test substances were determined graphically. They represent that concentration of test substance at which the specific binding of $^3$H-NMS to the muscarinic receptors in the various organs was inhibited by 50%. The results can be seen from Table 1.

B. Investigation of functional selectivity of the antimuscarinic effect

Substances with antimuscarinic properties inhibit the effects of agonists supplied exogenically or of acetylcholine, which is released from cholinergic nerve endings. The following is a description of some methods that are suitable for the detection of cardioselective antimuscarinic agents.

"In vivo" methods

The objective of the methods was to confirm the selectivity of the antimuscarinic effect. Those substances which had been selected on the basis of "in vitro" tests were tested for their
1. $M_1/M_2$ selectivity in the rat,
2. Salivation-inhibiting effect on the rat and
3. Inhibition of the acetylcholine effect on the bladder, bronchi and heart rate in the guinea pig.

1. $M_1/M_2$ selectivity in the rat

The method used was described by Hammer and Giachetti (Life Sciences 31, 2991-2998 (1982)). 5 minutes after the intravenous injection of increasing doses of the substance, either the right vagus was electrically stimulated (frequency: 25 Hz; pulse width: 2 ms; duration of stimulus: 30s; voltage: supramaximal) or 0.3 mg/kg of McN-A-343 were intravenously injected into male THOM rats. The bradycardia caused by vagus stimulation and the rise in blood pressure caused by McN-A-343 were determined. The dosage of the substances which reduced either the vagal bradycardia ($M_2$) or the rise in blood pressure ($M_1$) by 50% was determined graphically. For the results see Table II.

2. Salivation-inhibiting effect in the rat

Using the method of Lavy and Mulder (Arch. Int. Pharmacodyn. 178, 437-445, (1969)) male THOM rats anaesthetised with 1.2 g/kg of urethane were given increasing doses of the substance by i.v. route. The secretion of saliva was initiated by subcutaneous administration of 2 mg/kg of pilocarpine. The saliva was absorbed with blotting paper and the surface area covered was measured every 5 minutes by planimetry. The dosage of the substance which reduced the volume of saliva by 50% was determined graphically. For the results see Table II.

3. Inhibition of the effect of acetylcholine on the bladder, bronchi and heart rate in guinea pigs 5 minutes after the administration of the test substance, 10 microgram/kg of acetylcholine were simultaneously injected intravenously and intraarterially into anaesthetised guinea pigs. The heart rate was recorded directly by extracorporeal derivation of the ECG, the expiration resistance according to Konzett-Röbler and contraction of the exposed bladder. In order to determine the inhibition of the acetylcholine activity on the organs under investigation, dosage/activity curves were recorded and from them $-\log ED_{50}$ values were determined. For the results see Table III.

C. Investigations of possible effects on imipramine, histamine-H1 or serotonin-S2 receptors

Method (a) Studies of binding to the imipramine receptor

The organ donors were male Sprague-Dawley rats weighing from 180-220 g. The cerebral cortex was removed and homogenised in ice cold tris-HCl buffer (pH 7.5; 50 mM tris, 5 mM KCl) using an Ultra-Turrax. This homogenised material was washed 3 times and centrifuged for 10 minutes at 50,000×g. The pellets obtained were diluted in the ratio 1:125, compared with its starting weight. In the following binding mixture, this membrane preparation was incubated with 1 nM $^3$H-imipramine and a concentration series of test substances at 0° C. for 60 minutes.

Incubation was ended by rapid vacuum filtration. After the filters had been rinsed with buffer their radioactivity was measured. The proportion of non-specific binding was defined as the proportion of radioactivity in the presence of 100 micromolar desipramine. The $IC_{50}$ values were determined graphically. The results are shown in Table IV.

(b) Studies of binding to the serotonin-S2 receptor

For these tests, cerebral cortex tissue was taken in the same way as for the above study of binding to the imipramine receptor. Homogenisation was carried out in tris-HCl buffer (50 mM tris pH 7.7; 5.7 mM ascorbic acid) using an Ultra-Turrax. The homogenised material was then centrifuged at 50,000×g and the pellet was diluted in the ratio 1:250, based on the weight of the tissue. The incubation buffer in the binding mixture additionally contained 0.1 mM nialamide. Incubation was carried out at ambient temperature with 0.3 nM $^3$H-ketanserine and with a concentration series of the test substances for 60 minutes and then the mixtures were filtered in vacuo. The filters were then subjected to measurement of the radioactivity. The non-specific binding was determined using mixtures which additionally contain 3 micromolar ketanserine. They were evaluated in the same way as in the studies of binding to the imipramine receptor. The results are shown in Table IV.

(c) Studies of binding to the histamine-H1 receptor

In these tests, whole rat brains were used without the cerebellum. The tissue was homogenised in a phosphate buffer pH 7.5 according to Sörensen using the Ultra-Turrax. The homogenised material was then washed twice and centrifuged at 50,000×g. The pellet was taken up in a dilution, based on the starting tissue, of 1:100. The binding mixtures were incubated at ambient temperature with 2 nM $^3$H-pyrilamine and a series of concentrations of test substances for 60 minutes. The reactions were also ended by vacuum filtration and the radioactivity of the filters was measured. The non-specific binding was determined using mixtures which contained 10 micromolar triprolidine. The results were evaluated as in the studies of binding to the imipramine receptor. The results are shown in Table IV.

As examples, the following compounds were investigated according to the above information:
A=5,11-dihydro-11-[6-(1-piperidinyl)hexyl]-6H-pyrido[2,3-b][1,4]benzodiazepin-6-one B = 11-[4-[2-[(diethylamino)methyl]-1-piperidinyl]-butyl]-5,11-dihydro-6H-pyrido[2,3-b][1,4]benzodiazepin-6-one, C = 11-[4-[2-[(diethylamino)methyl]-1-piperidinyl]but-2-ynyl]-5,11-dihydro-6H-pyrido[2,3-b][1,4]benzodiazepin-6-one, and as comparison substances D = 11-[[2-[(diethylamino)methyl]-1-piperidinyl]acetyl]-5,11-dihydro-6H-pyrido[2,3-b][1,4]benzodiazepin-6-one (see U.S. Pat. No. 4,550,107).

E = 5,11-dihydro-11-[(4-methyl-1-piperazinyl)acetyl]-6H-pyrido[2,3-b][1,4]benzodiazepin-6-one (pirenzepine, see U.S. Pat. No. 3,660,380) and F = atropine The following Tables show the results found:

TABLE I

Receptor binding tests in vitro:
Results:

| Substance | Receptor binding test $IC_{50}$[nM] | | | Selectivity factors: | |
|---|---|---|---|---|---|
| | Cortex (C) | Heart (H) | Submandibular gland (SM) | $\frac{IC_{50} (SM)}{IC_{50} (H)}$ | $\frac{IC_{50} (C)}{IC_{50} (H)}$ |
| A | 4 | 0.6 | 10 | 16.7 | 6.7 |
| B | 20 | 2 | 80 | 40 | 10 |
| C | 200 | 18 | 700 | 38.9 | 11.1 |
| D | 1200 | 140 | 5000 | 36 | 8.6 |
| E | 100 | 1500 | 200 | 0.13 | 0.07 |
| F | 2 | 4 | 4 | 1 | 0.5 | nM = nanomolar.

The figures in Table I above show that the new compounds of the general formula I distinguish between muscarinic receptors from different tissues. This is clear from the considerably lower $IC_{50}$ values obtained when investigating preparations from the heart, compared with those from the cerebral cortex and submandibular gland. It should be pointed out that compounds A, B and C, whilst maintaining the same selectivity, show a considerably higher potency compared with compound D.

TABLE II $M_1/M_2$ selectivity and salivation-inhibiting activity on rat:
Results:

| Substance | $-\log ED_{50}$[mole · kg$^{-1}$] | | |
|---|---|---|---|
| | Heart | Blood pressure | Salivation inhibition |
| A | 7.96 | 6.53 | 6.35 |
| B | 7.40 | 6.17 | 5.50 |
| C | 7.52 | 5.96 | 5.12 |
| D | 6.42 | 5.63 | 5.00 |
| E | 5.60 | 6.94 | 6.22 |
| F | 7.04 | 7.34 | 7.60 |

TABLE III

Inhibition of acetylcholine activity on the bladder, bronchi and heart rate in the guinea pig:
Results:

| Substance | $-\log ED_{50}$[mole · kg$^{-1}$] | | |
|---|---|---|---|
| | Heart | Bronchi | Bladder |
| A | 7.18 | 7.07 | 5.89 |
| B | 6.33 | 6.19 | <5.00 |
| C | 6.61 | 5.80 | <5.64 |
| D | 5.84 | 5.58 | 4.73 |
| E | 5.85 | 6.57 | 5.36 |
| F | 7.70 | 7.96 | 7.03 |

TABLE IV

Influence on the imipramine, histamine-H1 and serotonin-S2 receptors.
Results:

| Substance | $IC_{50}$ (nM) | | |
|---|---|---|---|
| | Imipramine | S2 | H1 |
| A | 10 000 | 20 000 | 10 000 |
| B | 60 000 | 30 000 | 9 000 |
| C | 100 000 | 40 000 | 50 000 |
| Desipramine | 200 | | |
| Ketanserine | | 15 | |
| Pyrilamine | | | 7 |

The Table shows that the compounds mentioned have no effect on the imipramine, histamine-H1 or serotonin-S2 receptors in the concentrations which result in an inhibition in the muscarinic receptor. Therefore, when administered in therapeutic doses, the side effects connected with these receptors need not be expected.

The pharmacological data in Tables II and III above show—in total agreement with the receptor binding studies—that the heart rate is increased by the above-mentioned compounds even at dosages at which there is no restriction in the secretion of saliva.

Moreover, the pharmacological data in Table III above indicates a surprisingly high power of distinction between the heart and smooth muscle.

The above-mentioned substances show a substantially improved effectiveness compared with the known compound D. At the same time, their therapeutically useful selectivity is retained. This results in a reduction in the quantity of drug to be administered to the patient without increasing the risk of muscarinic side effects.

Furthermore, the compounds prepared according to the invention are well tolerated; even in the highest doses administered, no toxic side effects were observed in the pharmacological trials.

For pharmaceutical use, the compounds of general formula I may be incorporated in known manner into the conventional pharmaceutical preparation forms, e.g. solutions, suppositories, tablets, coated tablets, capsules or infusions. The daily dosage is generally between 0.02 and 5 mg/kg, preferably 0.02 and 2.5 mg/kg, particularly 0.05 and 1.0 mg/kg body weight, which is optionally administered in the form of several, preferably 1 to 3, individual doses, in order to achieve the desired results.

The following Examples are intended to illustrate the invention:

Satisfactory elemental analyses, IR, UV, $^1$H-NMR and in many cases mass spectra are available for all the compounds.

EXAMPLE 1

5,11-Dihydro-11-[4-(1-pyrrolidinyl)-but-2-ynyl]-6H-pyrido2,3-b][1,4]benzodiazepin-6-one (a)

5,11-Dihydro-11-(prop-2-ynyl)-6H-pyrido[2,3-b][1,4]benzodiazepin-6-one

To a suspension of 7.4 g (0.035 mol) of 5,11-dihydro-6H-pyrido[2,3-b][1,4]benzodiazepin-6-one in 150 ml of anhydrous tetrahydrofuran, 44.8 ml (approx. 0.07 mol) of a 15% solution of n-butyl-lithium in n-hexane was added dropwise with stirring at a reaction temperature of from 0° to +10° C. After it had all been added, the mixture was stirred for 30 minutes at ambient temperature before a solution of 4.16 g (0.035 mol) of 3-bromoprop-1-yne in 25 ml of anhydrous tetrahydrofuran was added dropwise. The resulting mixture was stirred for a further 2 hours at ambient temperature, added to 1 liter of saturated aqueous saline solution and the resulting mixture was extracted exhaustively with ethylacetate. The combined ethylacetate extracts were washed twice more with 100 ml of saturated saline solution, dried over sodium sulphate with the addition of 1 g of activated charcoal and evaporated down in vacuo. The residue was purified on silica gel by chromatography using dichloromethane/ethyl acetate 95/5 (v/v) as eluant. 8.5 g (97% of theory) of colourless crystals were obtained, m.p. 199° C. (decomposition).

(b)
5,11-Dihydro-11-[4-(1-pyrrolidinyl)-but-2-ynyl]-6H-pyrido[2,3-b][1,4]benzodiazepin-6-one The mixture of 8.5 g (0.034 mol) of 5,11-dihydro-11-(prop-2-ynyl)-6H-pyrido[2,3-b][1,4]benzodiazepin-6-one, 50 ml of anhydrous dioxan, 1.08 g (0.036 mol) of paraformaldehyde, 2.77 g (0.039 mol) of pyrrolidine and 0.2 g of copper (I) chloride was refluxed for 1 hour with stirring and then, after cooling, evaporated down in a water jet vacuum. The residue was partitioned between water and ethylacetate, the ethylacetate solution obtained was mixed with 2 g of animal charcoal, dried over sodium sulphate, filtered and evaporated down. The residue was purified by column chromatography on silica gel using first ethyl acetate and then dichloromethane/cyclohexane/methanol/conc. ammonia 68/15/15/2 (v/v/v/v) as eluant. The crude product obtained after evaporation of the suitable eluates was recrystallised once more from ethylacetate. Yield: 1.6 g (14% of theory) of colourless crystals, m.p. 153° C.; $R_F$ 0.5 (Merck, ready-made TLC plates, silica gel 60 F-254; eluant: dichloromethane/cyclohexane/methanol/conc. ammonia 68/15/15/2 v/v/v/v).

EXAMPLE 2

11-[4-[2-[(Diethylamino)methyl]-1-piperidinyl]but-2-ynyl]-5,11-dihydro-6H-pyrido[2,3-b][1,4]benzodiazepin-6-one Prepared analogously to Example (1b) from 5,11-dihydro-11-(prop-2-ynyl)-6H-pyrido[2,3-b][1,4]benzodiazepin-6-one, paraformaldehyde and 2-[(diethylamino)methyl]piperidine in a yield of 28% of theory. Colourless crystals, m.p. 132°-134° C.

EXAMPLE 3

Trans-5,11-dihydro-11-[4-[(4-hydroxy-cyclohexyl)methylamino]-but-2-ynyl]-6H-pyrido[2,3-b][1,4]benzodiazepin-6-one Prepared analogously to Example 1b) from 5,11-dihydro-11-(prop-2-ynyl)-6H-pyrido[2,3-b][1,4]benzodiazepin-6-one, paraformaldehyde and trans-(4-hydroxycyclohexyl)methylamine in a yield of 31% of theory. Colourless crystals, m.p. 183°-184° C. (after recrystallisation from ethyl acetate and methanol).

EXAMPLE 4

11-[4-[(Cyclohexyl)methylamino]-but-2-ynyl]-5,11-dihydro-6H-pyrido[2,3-b][1,4]benzodiazepin-6-one Prepared analogously to Example (1b) from 5,11-dihydro-11-(prop-2-ynyl)-6H-pyrido[2,3-b][1,4]benzodiazepin-6-one, paraformaldehyde and (cyclohexyl)methylamine in a yield of 17% of theory. Colourless crystals m.p. 133°-134° C. (diethyl ether).

EXAMPLE 5

5,11-Dihydro-11-[4-(1-piperidinyl)-but-2-ynyl]-6H-pyrido[2,3-b][1,4]benzodiazepin-6-one Prepared analogously to Example 1b) from 5,11-dihydro-11-(prop-2-ynyl)-6H-pyrido[2,3-b][1,4]benzodiazepin-6-one, paraformaldehyde and piperidine in a yield of 19% of theory. Colourless crystals m.p. 165°-168° C. (ethyl acetate). The hemifumarate melted at 198° C. (ethanol) with decomposition.

EXAMPLE 6

5,11-Dihydro-11-[6-(1-piperidinyl)hexyl]-6H-pyrido-[2,3-b][1,4]benzodiazepin-6-one To a suspension of 33.2 g (0.157 mol) of 5,11-dihydro-6H-pyrido[2,3-b][1,4]benzodiazepin-6-one in 875 ml of anhydrous dioxan, 173 ml (approx. 0.45 mol) of a 2.6 molar solution of n-butyl-lithium in n-hexane was added dropwise at ambient temperature and the resulting mixture was then stirred for another hour at the same temperature. It was then heated to 70° C. and at a reaction temperature of not more than 75° C. 83.0 g (0.034 mol) of 1-bromo6-(1-piperidinyl)hexane were added dropwise, then to complete the reaction the mixture was stirred for a further 4 hours at 80° C. After cooling, the solvent was distilled off in a water jet vacuum, the residue was adjusted to pH 7 with dilute aqueous hydrochloric acid and the mixture was then filtered. The filtrate was made alkaline with concentrated aqueous potassium hydroxide solution and extracted exhaustively with dichloromethane. The dichloromethane extracts were dried over sodium sulphate and then evaporated down and the residue remaining was digested with 100 ml of boiling diethyl ether and filtered while hot. The residue remaining after the ether had been removed was purified by chromatography on silica gel (Macherey-Nagel, 0.2-0.5 mm) using dichloromethane/methanol/cyclohexane/ethyl acetate/conc. ammonia 59/7.5/7.5/25/1 (v/v/v/v/v) as eluant. By evaporating the desired fractions and subsequently recrystallising from acetonitrile, a colourless crystalline product with a m.p. of 131° to 132° C. was obtained in a yield of 11.29 g (19% of theory). The hydrochloride melted at 223° C. (ethanol).

EXAMPLE 7

5,11-Dihydro-11-[4-(4-morpholinyl)-but-2-ynyl]-6H-pyrido[2,3-b][1,4]benzodiazepin-6-one Prepared analogously to Example 1b) from 5,11-dihydro-11-(prop-2-ynyl)-6H-pyrido[2,3-b][1,4]benzodiazepin-6-one, paraformaldehyde and morpholine in a yield of 19% of theory. Colourless crystals, m.p. 168° C.

EXAMPLE 8

11-[4-[2-[(Diethylamino)methyl]-1-piperidinyl]butyl]-5,11-dihydro-6H-pyrido[2,3-b][1,4]benzodiazepin-6-one 4.3 g (0.01 mol) of 11-[4-[2-[(diethylamino)methyl]-1-piperidinyl]-but-2-ynyl]-5,11-dihydro-6H-pyrido[2,3-b][1,4]benzodiazepin-6-one were dissolved in 40 ml of ethanol and after the addition of 0.5 g of 10% palladium on animal charcoal the mixture was hydrogenated under 3 bar of hydrogen pressure and at ambient temperature until the uptake of hydrogen had ceased. The mixture was filtered, the filtrate was evaporated down in a water jet vacuum and the oily residue remaining was purified by column chromatography on silica gel (Macherey-Nagel 60, 0.063–0.2 mm) using firstly ethyl acetate, then ethyl acetate/methanol/conc. ammonia 90/10/2 as eluant. From the fractions, after evaporation of the solvent and recrystallisation of the residue from diisopropyl ether, colourless crystals were obtained, m.p. 112° C., $R_F$ 0.75 (Merck, ready-made TLC plates, silica gel 60F-254; eluant: dichloromethane/cyclohexane/methanol/conc. ammonia 68/15/15/2 v/v/v/v). Yield: 2.2 g (50.5% of theory).

EXAMPLE 9

11-[4-[2-[[(Cyclohexyl)methylamino]methyl]-1-piperidinyl]-but-2-ynyl]-5,11-dihydro-6H-pyrido[2,3-b][1,4]benzodiazepin-6-one Prepared analogously to Example 1b) from 5,11-dihydro-11-(prop-2-ynyl)-6H-pyrido[2,3-b][1,4]benzodiazepin-6-one, paraformaldehyde and 2-[[(cyclohexyl)methylamino]methyl]piperidine in a yield of 34% of theory. The monohydrochloride melted at 205° C. (decomp.).

EXAMPLE 10

5,11-Dihydro-11-[4-(hexahydro-1H-1-azepinyl)-but-2-ynyl]-6H-pyrido[2,3-b][1,4]benzodiazepin-6-one Prepared analogously to Example 1b) from 5,11-dihydro-11-(2-propynyl)-6H-pyrido[2,3-b][1,4]benzodiazepin-6-one, paraformaldehyde and hexahydro-1H-azepine in a yield of 35% of theory. Colourless crystals m.p. 157° C. (ethyl acetate).

EXAMPLE 11

5,11-Dihydro-11-[4-(hexahydro-1H-1-azepinyl)-butyl]-6H-pyrido2,3-b][1,4]benzodiazepin-6-one Prepared analogously to Example 8 from 5,11-dihydro-11-[4-(hexahydro-1H-1-azepinyl)-but-2-ynyl]-6H-pyrido[2,3-b][1,4]benzodiazepin-6-one in a yield of 74% of theory. Colourless crystals m.p. 99°–101° C. (ether/-diisopropyl ether 1/1 v/v).

EXAMPLE 12

5,11-Dihydro-11-6-(4-methyl-1-piperazinyl)-hexyl]-6H-pyrido[2,3-b][1,4]benzodiazepin-6-one Prepared analogously to Example 6 from 5,11-dihydro-6H-pyrido[2,3-b][1,4]benzodiazepin-6-one, n-butyllithium and 1-bromo-6-(4-methyl-1-piperazinyl)-hexane in a yield of 16% of theory. Colourless crystals m.p. 149°–150° C. (from acetonitrile using activated charcoal).

EXAMPLE 13

5,11-Dihydro-11-[4-(1-piperidinyl)butyl]-6H-pyrido[2,3-b][1,4]benzodiazepin-6-one Prepared analogously to Example 8 from 5,11-dihydro-11-[4-(1-piperidinyl)-but-2-ynyl]-6H-pyrido[2,3-b][1,4]benzodiazepin-6-one in a yield of 35% of theory. Colourless crystals, m.p. 131°–132° C. (ethyl acetate).

EXAMPLE 14

5,10-Dihydro-5-[6-(1-piperidinyl)-hexyl]-11H-dibenzo[b,e][1,4]diazepin-11-one

Prepared analogously to Example 6 from 5,10-dihydro-11H-dibenzo[b,e][1,4]diazepin-11-one, n-butyllithium and 1-bromo-6-(1-piperidinyl)-hexane in a yield of 46% of theory. Colourless crystals, m.p. 124°–125° C. (from acetonitrile using activated charcoal).

EXAMPLE 15

5,10-Dihydro-5-[6-(4-methyl-1-piperazinyl)hexyl]-11H-dibenzo[b,e][1,4]diazepin-11-one dihydrochloride Prepared analogously to Example 6 from 5,10-dihydro-11H-dibenzo[b,e][1,4]diazepin-11-one, n-butyllithium and 1-bromo-6-(4-methyl-1-piperazinyl)hexane in a yield of 18% of theory. The dihydrochloride melted at 232°–234° C. (acetonitrile/ethanol 1/1 v/v).

By chromatographic purification, a colourless crystalline by-product with a melting point of 124°–126° C. (diisopropyl ether/acetonitrile 9/1 v/v) was isolated in a yield of 4% of theory, this compound being found to be 5,10-dihydro-5-[6-[4-[2-(1,3-dioxolan-2-yl)ethyl]-1-piperazinyl]hexyl]-11H-dibenzo[b,e][1,4]diazepin-11-one, according to IR, UV, $^1$H-NMR and mass spectra.

EXAMPLE 16

5,10-Dihydro-5-[6-(hexahydro-1H-1-azepinyl)hexyl]-11H-dibenzo[b,e][1,4]diazepin-11-one hydrochloride Prepared analogously to Example 6 from 5,10-dihydro-11H-dibenzo[b,e][1,4]diazepin-11-one, n-butyllithium and 1-bromo-6-(hexahydro-1H-1-azepinyl)hexane in a yield of 15% of theory. The monohydrochloride, which is sparingly soluble in water, melted at 103°–105° C. (from acetonitrile using activated charcoal).

EXAMPLE 17

5,10-Dihydro-5-[6-(1-pyrrolidinyl)hexyl]-11H-dibenzo[b,e][1,4]diazepin-11-one hydrochloride Prepared analogously to Example 6 from 5,10-dihydro-11H-dibenzo[b,e][1,4]diazepin-11-one, n-butyllithium and 1-bromo-6-(1-pyrrolidinyl)hexane in a yield of 25% of theory. The water-soluble monohydrochloride melted at 185°–188° C. (acetonitrile).

EXAMPLE 18

5,11-Dihydro-11-[6-(1-piperidinyl)hexyl]-6H-pyrido[2,3-b][1,4]benzodiazepin-6-one 24.1 g (0.08 mol) of 5,11-dihydro-5-(phenylmethyl)-6H-pyrido[2,3-b][1,4]benzodiazepin-6-one (m.p. 152°–154° C.) were dissolved in 180 ml of anhydrous dimethylformamide, then 2.88 g (0.096 mol) of an 80% sodium hydride dispersion in mineral oil were added at ambient temperature and the resulting mixture was stirred for 45 minutes at 60° C. Then 23.8 g (0.096 mol) of 1-bromo-6-(1-piperidinyl)hexane were added dropwise and the mixture was heated to 120° C. for 30 minutes. After evaporation in vacuo, the residue was partitioned between dichloromethane and 5% aqueous hydrochloric acid, the aqueous phase was separated off and made alkaline with sodium hydroxide. The oil separated was taken up in dichloromethane, the solvent was distilled off in a water jet vacuum, the oily, highly viscous residue was carefully stirred with 250 g of 100% orthophosphoric acid and 7.5 g of phenol and the resulting mixture was heated to 120° C. for 3 hours. The mixture cooled to 70° C. was stirred into 2 kg of crushed ice, then made significantly alkaline by the addition of caustic soda and extracted exhaustively with dichloromethane. The dichloromethane extracts were dried over sodium sulphate and evaporated down, the residue remaining was digested with 10 ml of boiling ether and filtered while hot. The ether was evaporated off, the residue was purified by chromatography on silica gel (Macherey-Nagel, 0.2–0.5 mm) using dichloromethane/methanol/cyclohexane/ethyl acetate/conc. ammonia 59/7.5/7.5/25/1 (v/v/v/v/v) as eluant. By evaporating the appropriate fractions and subsequent recrystallisation from acetonitrile, colourless crystals with a melting point of 131°–132° C. were obtained in a yield of 21.8 g (72% of theory) which were found, according to their mixed melting point, thin layer chromatogram, IR, UV., $^1$H-NMR spectra, to be totally identical to a preparation prepared according to Example 6.

EXAMPLE 19

5,11-Dihydro-11-[7-(1-piperidinyl)heptyl]-6H-pyrido[2,3-b][1,4]benzodiazepin-6-one Prepared analogously to Example 18 by reacting 5,11-dihydro-5-(phenylmethyl)-6H-pyrido[2,3-b][1,4]benzodiazepin-6-one with 1-bromo-7-(1-piperidinyl)-heptane in the presence of sodium hydride and dimethylformamide and subsequent acidolytic cleaving of the phenylmethyl group by heating with 80% polyphosphoric acid in the presence of phenol. Yield: 17% of theory. Colourless crystals m.p. 118°–120° C. (after recrystallisation from diisopropyl ether and cyclohexane).

EXAMPLE 20

4,9-Dihydro-3-methyl-4-[6-(4-methyl-1-piperazinyl)-hex-4-ynyl]-10H-thieno[3,4-b][1,5]benzodiazepin-10-one (a)

4,9-Dihydro-3-methyl-4-(prop-2-ynyl)-10H-thieno[3,4-b][1,5]benzodiazepin-10-one

Prepared analogously to Example 1a) from 4,9-dihydro-3-methyl-10H-thieno[3,4-b][1,5]benzodiazepin-10-one and 3-bromo-prop-1-yne in the presence of butyllithium and tetrahydrofuran in a yield of 50% of theory. The crude crystalline product was used for subsequent reactions without being further purified by chromatography.

(b)

4,9-Dihydro-3-methyl-4-[6-(4-methyl-1-piperazinyl)-hex-4-ynyl]-10H-thieno3,4-b][1,5]benzodiazepin-10-one Prepared analogously to Example 1b) from 4,9-dihydro-3-methyl-4-(prop-2-ynyl)-10H-thieno[3,4-b][1,5]benzodiazepin-10-one, paraformaldehyde and N-methylpiperazine in the presence of copper(I)chloride in a yield of 17% of theory. The colourless hydrochloride melted at 178° C. (decomp.).

EXAMPLE 21

4,9-Dihydro-4-[6-(hexahydro-1H-1-azepinyl)-hex-4-ynyl]-3-methyl-10H-thieno[3,4-b]1,5]benzodiazepin-10-one Prepared analogously to Example (1b) from 4,9-dihydro-3-methyl-4-(prop-2-ynyl)-10H-thieno[3,4-b][1,5]benzodiazepin-10-one, paraformaldehyde and hexamethyleneimine in the presence of copper(I)chloride in a yield of 3% of theory. The colourless monohydrochloride melted at 169°–172° C.

EXAMPLE 22

4,9-Dihydro-3-methyl-4-[6-[4-(phenylmethyl)-1-piperazinyl]-hex-4-ynyl]-10H-thieno[3,4-b][1,5]benzodiazepin-10-one Prepared analogously to Example 1b) from 4,9-dihydro-3-methyl-4-(prop-2-ynyl)-10H-thieno[3,4-b][1,5]benzodiazepin-10-one, paraformaldehyde and N-(phenylmethyl)piperazine in the presence of copper-(I)chloride in a yield of 12% of theory. $R_F$ 0.5 (Merck, readymade TLC plates, silica gel 60F-254; eluant: dichloromethane/ethanol 9/1 v/v).

EXAMPLE 23

4,9-Dihydro-3-methyl-4-[6-[4-(2-phenyl-ethyl)-1-piperazinyl]-hex-4-ynyl]-10H-thieno[3,4-b][1,5]benzodiazepin-10-one.

Prepared analogously to Example 1b) from 4,9-dihydro-3-methyl-4-(prop-2-ynyl)-10H-thieno[3,4-b][1,5]benzodiazepin-10-one, paraformaldehyde and N-(2-phenylethyl)piperazine in the presence of catalytic quantities of copper(I)chloride in a yield of 17% of theory. The colourless monohydrochloride melted at 223°–225° C. with decomposition; $R_F$ 0.8 (Merck, ready-made TLC plates, silica gel 60 F-254; eluant: ethyl acetate/methanol/cyclohexane/conc. ammonia 8/1/1/0.1 v/v/v/v).

The following Examples illustrate the preparation of some pharmaceutical administration forms:

EXAMPLE I

Tablets containing 5 mg of 5,11-dihydro-11-[6-(1-piperidinyl)hexyl]-6H-pyrido[2,3-b][1,4]benzodiazepin-6-one

| Composition | |
| --- | --- |
| 1 tablet contains | |
| Active substance | 5.0 mg |
| Lactose | 148.0 gm |
| Potato starch | 65.0 gm |
| Magnesium stearate | 2.0 mg |
| | 220.0 mg |

Method of preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.
Weight of tablet: 220 mg
Punch: 9 mm

EXAMPLE II

Coated tablets containing 1.5 mg of 5,11-dihydro-11-[6-(1-piperidinyl)hexyl]-6H-pyrido[2,3-b][1,4]-benzodiazepin-6-one The tablets prepared according to Example I are coated, by a known method, with a coating consisting essentially of sugar and talc. The finished coated tablets are polished with beeswax.
Weight of coated tablet: 300 mg

EXAMPLE III

Ampoules containing 10 mg of
11-[4-[2-[(diethylamino)methyl]-1-piperidinyl]butyl]-
5,11-dihydro-6H-pyrido[2,3-b][1,4]benzodiazepin-6-one

| Composition | |
|---|---|
| 1 ampoule contains | |
| Active substance | 10.0 mg |
| Sodium chloride | 8.0 mg |
| Distilled water ad | 1.0 ml |

Method of preparation

The active substance and sodium chloride are dissolved in distilled water and then made up to the volume specified. The solution is sterile filtered and transferred into 1 ml ampoules.
Sterilisation: 20 minutes at 120° C.

EXAMPLE IV

Suppositories containing 20 mg of
5,11-dihydro-11-6-(1-piperidinyl)-hexyl]-6H-pyrido[2,3-b][1,4]benzodiazepin-6-one

| Composition | |
|---|---|
| 1 suppository contains | |
| Active substance | 20.0 mg |
| Suppository mass (e.g. Witepsol W 45 ®) | 1680.0 mg |
| | 1700.0 mg |

Method of preparation

The finely powdered active substance is suspended in the molten suppository mass which has been cooled to 40° C. The mass is poured at 37° C. into slightly chilled suppository moulds.
Weight of suppository 1.7 g

EXAMPLE V

Drops containing
5,11-dihydro-11-[6-(1-piperidinyl)hexyl]-6H-pyrido[2,3-b][1,4]benzodiazepin-6-one

| Composition | |
|---|---|
| 100 ml of drops solution contain | |
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water ad | 100.0 ml |

Method of preparation

The active substance and sodium cyclamate are dissolved in about 70 ml of water and glycerol is added. The p-hydroxybenzoates, aniseed oil and menthol are dissolved in ethanol and this solution is added with stirring to the aqueous solution. Finally, the solution is made up to 100 ml with water and filtered to remove any suspended particles.

What is claimed is:
1. A condensed diazepinone of the formula:

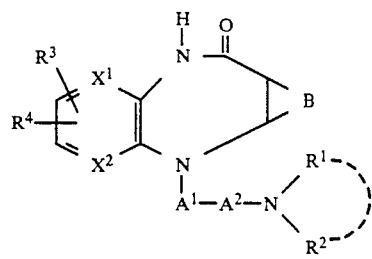

wherein
B is one of the divalent groups

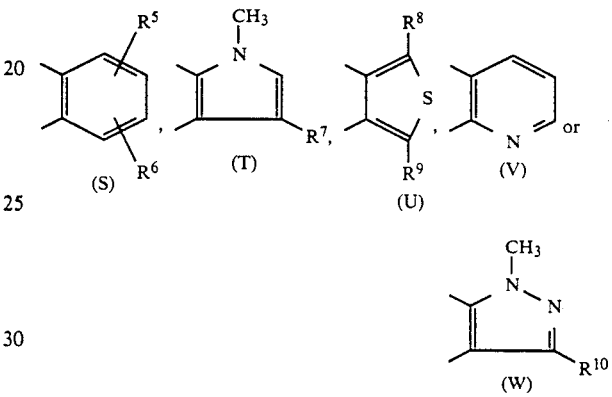

$X^1$ and $X^2$ each are a =CH— group; or, if B is the divalent group (S), (U) or (W), $X^1$ and $X^2$ each are a nitrogen or a =CH— group, with the proviso that only one of $X^1$ and $X^2$ can be a =CH— group;

$A^1$ is a methylene group, unsubstituted or substituted by one or two methyl groups;

$A^2$ is a straight-chained alkylene of 3 to 7 carbon atoms, unsubstituted or methyl-substituted; or $A^2$ is a straight-chained alkylene group of 3 to 7 carbon atoms comprising a double or triple bond, unsubstituted or methyl-substituted;

$R^1$ is a branched or unbranched alkl group of 1 to 4 carbon atoms;

$R^2$ is a branched or unbranched alkyl group of 1 to 7 carbon atoms, unsubstituted or substituted by a hydroxy group at its 2nd to 7th carbon atoms; or $R^2$ is a cycloalkyl or cycloalkylmethyl group with 3 to 7 carbon atoms in the cycloalkyl ring, which cycloalkyl ring is unsubstituted or substituted by a hydroxy group; or $R^1$ and $R^2$ together with the intervening nitrogen atom, are a pyrrolidino or morpholino group, a piperido group, a piperidino group substituted with a dialkylaminomethyl or a cycloalkylmethylaminomethyl group, a hexahydro-1H-azepino group or a piperazino group substituted by an alkyl or phenylalkyl group, wherein the alkyl moieties comprise 1 to 4 carbon atoms and wherein the cycloalkyl moieties comprise 4 to 7 carbon atoms;

$R^3$ is hydrogen, chlorine, or an alkyl group of 1 to 4 carbon atoms;

$R^4$ is hydrogen or a methyl group;

$R^5$ and $R^6$ each are hydrogen, fluorine, chlorine, bromine, or an alkyl group of 1 to 4 carbon atoms;

$R^7$ is hydrogen, chlorine, or a methyl group;

$R^8$ is hydrogen or an alkyl group of 1 to 4 carbon atoms;

$R^9$ is hydrogen, halogen or an alkyl group of 1 to 4 carbon atoms; and $R^{10}$ is a hydrogen or a methyl group, wherein, if B is the divalent group (T) and $R^7$ is a hydrogen atom, $R^3$ cannot be chlorine and $A^2$ cannot contain any double or triple bonds, and the diastereomeric and enantiomeric forms thereof and the physiologically acceptable salts thereof and inorganic or organic acids.

2. A condensed diazepinone as recited in claim 1, wherein $X^1$ is a =CH— group;

$X^2$ is nitrogen and B is the divalent group (S), $R^3$, $R^4$ and $R^5$ each are hydrogen, and $R^6$ is hydrogen, chlorine, bromine, or a methyl or ethyl group in the 8 or 9-position of the heterocyclic ring, or $X^2$ is a =CH— group and B is the divalent group (U) or (V), $R^8$ is hydrogen and $R^9$ is a methyl;

$A^1$ is a methylene group;

$A^2$ is a straight-chained alkylene chain of 3 to 6 carbon atoms; or $A^2$ is a straight-chained alkylene group of 3 to 6 atoms comprising a double or triple bond;

$R^1$ is a branched or unbranched alkyl group of 1 to 4 carbon atoms;

$R^2$ is a branched or unbranched alkyl group of 1 to 7 carbon atoms, a cycloalkyl group or a (cycloalkyl)-methyl group, wherein the cycloalkyl ring is unsubstituted or substituted by a hydroxy group, and wherein the cycloalkyl ring comprises 3 to 7 carbon atoms, or $R^1$ and $R^2$ together with the intervening nitrogen atom are a pyrrolidino or morpholino group, a piperidino group, a piperidino group substituted by a dialkylaminomethyl or a cycloalkylmethylaminomethyl group, a hexahydro-1H-azepino group or a piperazino group substituted with an alkyl or phenylalkyl group, wherein the alkyl moieties comprise 1 to 4 carbon atoms and wherein the cycloalkyl moieties comprise 4 to 7 carbon atoms, and the diastereomeric and enantiomeric forms thereof and the physiologically acceptable salts thereof with inorganic or organic acids.

3. A condensed diazepinone as recited in claim 2, wherein:

$X^2$ is nitrogen; B is the divalent group (S); $R^3$, $R^4$ and $R^5$ are hydrogen; and $R^6$ is hydrogen, chlorine, bromine, or a methyl or ethyl group in the 8- or 9-position of the heterocyclic ring;

$R^1$ and $R^2$ together with the intervening nitrogen atom are a dimethylamino, diethylamino, dipropylamino, [bis(methylethyl)]amino, 1-pyrrolidinyl, 1-piperidinyl, hexahydro-1H-1-azepinyl, 4-morpholinyl, 2-[(diethylamino)methyl]-1-piperidinyl, trans-(4-hydroxy-cyclohexyl)methylamino, (cyclohexyl)methylamino, 2-[[(cyclohexyl)methylamino]methyl]-1-piperidinyl, 4-methyl-1-piperazinyl, 4-[2-(1,3-dioxolan-2-yl)ethyl]-1-piperazinyl, 4-(phenylmethyl)-1-piperazinyl or 4-(2-phenylethyl)-1-piperazinyl group, and the diastereomeric and enantiomeric forms thereof and the physiologically acceptable salts thereof with inorganic or organic acids.

4. 5,11-dihydro-11-[6-(1-piperidinyl)hexyl]-6H-pyrido-[2,3b-][1,4]benzodiazepin-6-one.

5. 11-[4-[2-[(diethylamino)methyl]-1-piperidinyl]-butyl]- 5,11-dihydro-6H-pyrido[2,3-b][1,4]benzodiazepin-6-one.

6. 11-[4-[2-[(diethylamino)methyl]-1-piperidinyl]-but-2-ynyl]-5,11-dihydro-6H-pyrido[2,3-b][1,4]benzodiazepin-6-one.

7. A pharmaceutical composition useful as vagal pacemaker for treatment of bradycardia an bradyarrhythmia which comprises a therapeutically effective amount of the condensed diazepinone of claim 1.

8. A pharmaceutical composition useful as vagal pacemaker for treatment of bradycardia an bradyarrhythmia which comprises a therapeutically effective amount of the condensed diazepinone of claim 2.

9. A pharmaceutical composition useful as vagal pacemaker for treatment of bradycardia an bradyarrhythmia which comprises a therapeutically effective amount of the condensed diazepinone of claim 3.

10. A pharmaceutical composition useful as vagal pacemaker for treatment of bradycardia an bradyarrhythmia which comprises a therapeutically effective amount of the condensed diazepinone of claim 4.

11. A pharmaceutical composition useful as vagal pacemaker for treatment of bradycardia an bradyarrhythmia which comprises a therapeutically effective amount of the condensed diazepinone of claim 5.

12. A pharmaceutical composition useful as vagal pacemaker for treatment of bradycardia an bradyarrhythmia which comprises a therapeutically effective amount of the condensed diazepinone of claim 6.

13. A pharmaceutical composition with spasmolytic properties on peripheral organs, which comprises a spasmolytically effective amount of the condensed diazepinone of claim 1.

14. An antiemetic pharmaceutical composition which comprises an antiemetically effective amount of the condensed diazepinone of claim 1.

15. A pharmaceutical composition capable of promoting cerebral blood flow which comprises a cerebral blood flow promoting effective amount of the condensed diazepinone of claim 1.

16. A pharmaceutical composition useful as a treatment for diseases of the central nervous system which comprises a therapeutically effective amount of a condensed diazepinone of claim 1.

17. A pharmaceutical composition as recited in claim 16 wherein the composition is useful as a treatment for Alzheimer's disease or Parkinson's disease.

* * * * *